(12) United States Patent
Kube et al.

(10) Patent No.: US 10,390,760 B2
(45) Date of Patent: Aug. 27, 2019

(54) CARRIER SYSTEM FOR A MEDICAL DEVICE WORN ON THE BODY

(71) Applicant: ROCHE DIABETES CARE, INC., Indianapolis, IN (US)

(72) Inventors: Oliver Kube, Worms (DE); Helmut Walter, Heppenheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 229 days.

(21) Appl. No.: 15/412,531

(22) Filed: Jan. 23, 2017

(65) Prior Publication Data

US 2017/0128010 A1    May 11, 2017

Related U.S. Application Data

(63) Continuation of application No. PCT/EP2015/067223, filed on Jul. 28, 2015.

(30) Foreign Application Priority Data

Jul. 28, 2014    (EP) ..................................... 14178705

(51) Int. Cl.
  *A61B 5/00*    (2006.01)
  *A61B 5/145*    (2006.01)
  (Continued)

(52) U.S. Cl.
  CPC .......... *A61B 5/6833* (2013.01); *A61B 5/0476* (2013.01); *A61B 5/14503* (2013.01);
  (Continued)

(58) Field of Classification Search
  CPC ... A61L 24/046; A61L 24/06; B29C 65/4845; B29C 65/4825; A61F 13/0256;
  (Continued)

(56) References Cited

U.S. PATENT DOCUMENTS

2004/0074060 A1*  4/2004  Browne ............. A44B 18/0003
                                                         24/442
2007/0299405 A1  12/2007  Kaufmann et al.
(Continued)

FOREIGN PATENT DOCUMENTS

EP           1 832 261 A2    9/2007
WO    WO 2008/139816 A1    11/2008
(Continued)

OTHER PUBLICATIONS

English translation of International Preliminary Report on Patentability, PCT/EP2015/067223, dated Dec. 23, 2016.

*Primary Examiner* — Amber R Stiles
(74) *Attorney, Agent, or Firm* — Bose McKinney & Evans LLP

(57) ABSTRACT

This disclosure concerns a carrier system for a medical device worn on the body comprising a flexible carrier plaster which has a flat carrier layer and an adhesive coating thereon consisting of a pressure sensitive adhesive which adheres on the skin of a body part, and further comprising a platform which is positioned on the upper side of the carrier layer for mounting the device, wherein the platform has a bottom joining area which is joined to the upper side of the carrier layer by means of a structural adhesive which is applied as a bead along predefined adherend tracks.

20 Claims, 4 Drawing Sheets

(51) Int. Cl.
*A61F 13/02* (2006.01)
*A61B 5/0476* (2006.01)
*A61M 5/142* (2006.01)
*A61F 13/00* (2006.01)

(52) U.S. Cl.
CPC ........ *A61B 5/14532* (2013.01); *A61F 13/023* (2013.01); *A61M 5/14248* (2013.01); *A61F 2013/00412* (2013.01)

(58) Field of Classification Search
CPC .............. A61F 13/0226; A61F 13/0223; A61F 13/0213; A61F 13/0259; A61F 13/0206; A61F 2013/00412; A61F 13/023; A61M 5/14248; A61M 2205/02; A61B 2562/12; A61B 2560/0443; A61B 5/0476; A61B 5/14532; A61B 5/14503; B29L 2031/753
See application file for complete search history.

(56) References Cited

U.S. PATENT DOCUMENTS

| | | | |
|---|---|---|---|
| 2009/0130361 A1* | 5/2009 | Arnal | B29C 66/21 428/41.8 |
| 2010/0063438 A1* | 3/2010 | Bengtsson | A61M 5/14248 604/66 |
| 2010/0198183 A1* | 8/2010 | Lanigan | A61M 5/1413 604/406 |
| 2011/0160548 A1 | 6/2011 | Forster | |
| 2013/0190655 A1 | 7/2013 | Jackson et al. | |
| 2014/0114158 A1 | 4/2014 | Brister et al. | |
| 2014/0303521 A1 | 10/2014 | Nakamura et al. | |
| 2016/0213322 A1 | 7/2016 | Goldberg et al. | |

FOREIGN PATENT DOCUMENTS

WO    WO 2013/073311 A1    5/2013
WO    WO 2015/052288 A1    4/2015

* cited by examiner

CARRIER SYSTEM FOR A MEDICAL DEVICE WORN ON THE BODY

RELATED APPLICATIONS

This application is a continuation PCT/EP2015/067223, filed Jul. 28, 2015, which claims priority to EP 14 178 705.1, filed Jul. 28, 2014, both of which are hereby incorporated herein by reference in their entireties.

BACKGROUND

The invention concerns a carrier system for a medical device worn on the body comprising a flexible carrier plaster which has a flat carrier layer and an adhesive coating thereon consisting of a pressure sensitive adhesive which adheres on the skin of a body part, and further comprising a dimensionally stable platform which is positioned on the upper side of the carrier layer facing away from the skin for mounting the device. The invention further concerns a particular use of such a carrier system.

In the area of medical technology in the field of continuous glucose monitoring (CGM), insulin delivery systems (IDS) and electroencephalography (EEG) it is known to connect a carrier plaster with the body worn instrument or probe by means of ultrasonic welding. In this connection a wearing period of several days is intended. However, ultrasonic welding often leads to early failure. Due to punctually induced heat the material of the carrier layer may slightly melt, which leads to local deterioration of the effective adhering area and internal stresses in the adherent film or coating of the visco-elastic system. As a result, the carrier plaster inadvertently detaches from the body. This is often the case in the joining area under the instrument, though this area should rather adhere particularly strong to fulfil the intended function, e.g., contact adhesion of a skin electrode.

SUMMARY

This disclosure further improves the known systems and achieves an improved efficiency for reliable, long-term use and at the same time uncomplicated handling.

This disclosure is based on the idea of providing a connection type which impairs the adhesive coating of the plaster (patch) as little as possible. Correspondingly, it is proposed according to this disclosure that the platform has a bottom joining area which is joined to the upper side of the carrier layer by means of a structural adhesive which is applied as a bead along predefined adherend tracks. Thereby, a full-faced connection under the instrument is avoided, preserving the flexibility of the plaster as much as possible. The combination of a pattern of structural adhesive beads with the full-faced adhesive coating of the carrier layer surprisingly has proved to lead to exceptional stability under typical loads on the skin.

In a specific embodiment, the adherend tracks are formed as a continuous line or dot-dashed line or line of points. If necessary, the line shape can vary in different in sections.

Another embodiment provides that the platform has an access port which is open to the skin through the carrier plaster. In the area of the port, a secure fixation must be provided, while allowing greater flexibility in other zones. In this context, a further improvement can be achieved when an adherend track is formed circumferentially around the access port.

Another particularly advantageous embodiment provides that one or more adherend tracks run radially or star-shaped as viewed from the access port, thus securing the entire joining area while keeping intermediate sections free.

It is also conceivable that at least one adherend track is arranged at a distance to the access port and/or runs only in a boundary range of the joining area.

In order to preserve larger flexible areas it is advantageous when the access port and a circular or line-shaped track are arranged at a distance to each other in different regions of the joining area, preferably symmetric to the center of the joining area.

Another particularly advantageous embodiment provides that the adherend tracks are positioned on the joining area such that the carrier layer preserves a stretchability which is increased in a preferred direction. In case the carrier layer has an anisotropic elasticity, a preferred direction of increased stretchability induced by the arrangement of the adherent tracks should be oriented in direction of the increased elasticity of the carrier layer.

With regard to the use on the skin, a preferred direction of increased stretchability of the carrier plaster is advantageously provided in the main direction of skin elongation at the application site on the body.

For a further improvement in convenience, it is advantageous when a marker is provided to indicate a preferred orientation of the carrier plaster to the user.

In a further embodiment, the carrier plaster has a circumferential border section which protrudes by at least 4 mm over the lateral margin of the joining area, thus avoiding unintentional peeling off.

For a further improvement of the operating life, it is advantageous when the structural adhesive has a shear strength of more than 1 N/mm$^2$.

Advantageously, the structural adhesive is formed by one of epoxide resin, cyanoacrylate and polyurethane-adhesives.

Further advantageously, the structural adhesive forms a permanent composite which can be dismantled only destructively. In contrast thereto, pressure sensitive adhesives, usually in the form of tapes, cannot be classified as structural adhesives due to their low peel and shear strength and their tendency to creep under load.

For further improvement of skin breathability, it is also advantageous when the platform has a perforated base or includes a membrane as a base material.

This disclosure also concerns use of the carrier system on the skin of a body part, wherein a preferred direction of increased stretchability of the carrier plaster is oriented in the main direction of skin elongation at the application site on the body.

The carrier system is preferably designed for at least one application of the following group:
sensory control or detection of a body parameter;
application of agents, specifically insulin through or to the skin,
provision of access to the body.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

Figure 1:
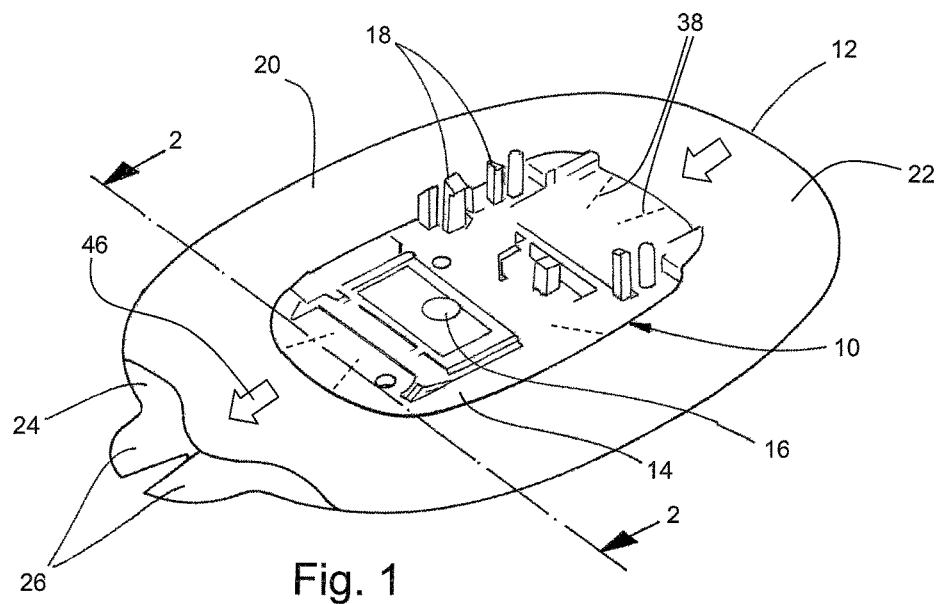
FIG. 1 is a perspective view of a carrier system including a plaster and a platform for a medical device for adhesive fixation to the skin.

The embodiments described below are not intended to be exhaustive or to limit the invention to the precise forms disclosed in the following description. Rather, the embodiments are chosen and described so that others skilled in the art may appreciate and understand the principles and practices of this disclosure.

Referring to the drawings, a carrier system 10 for adhesive fixation of a medical device or instrument worn on the body for long-term diagnostic applications comprises a flexible carrier plaster 12 and a dimensionally stable platform 14 which is mounted on the upper side of the carrier plaster 12 and has an access port 16 aligned with a hole in the carrier plaster 12.

As further illustrated in FIG. 1, the platform 14 is provided with form-locking elements 18 for mounting the device, which can include an infusion needle projecting through the access port 16 into the skin (not shown). It is also conceivable that the mounting platform forms an integral part of the device. Further details of such infusion devices for continuous glucose control may be found in U.S. Publication No. 2007/0299405, which is incorporated by reference herein. In other applications an instrument mounted on the platform 12 comprises a sensor or an electronic component such as an RFID-chip.

In the illustrated embodiment the platform is designed as a plate-like molded component, e.g., formed from polycarbonate. The plaster 12 comprises a substantially flat carrier layer 20 cut from a fabric and has a circumferential border section 22 protruding over the lateral rim of the platform 14. Prior to use, the self-adhesive bottom side of the plaster 12 is covered by a split liner 24 which can be easily removed by means of projecting pull flaps 26.

Figure 2:
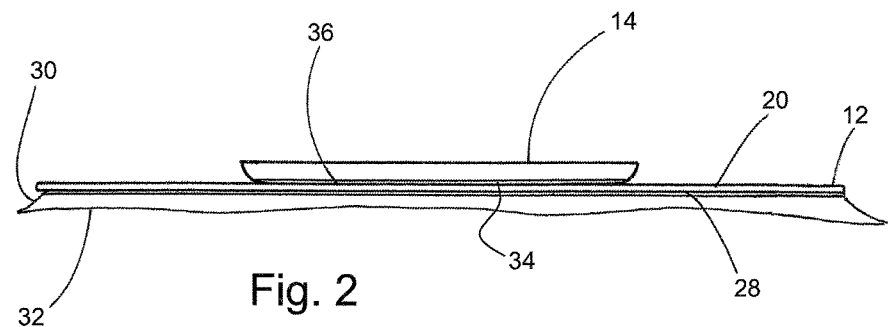
FIG. 2 is a sectional view along the line 2-2 of FIG. 1.

As can be seen best from FIG. 2, the carrier layer 20 of the plaster 12 is coated on its skin-facing bottom side with a coating 28, which is a pressure sensitive adhesive which adheres on the skin 30 of a body part 32 by applying pressure. On the opposite upper side, the carrier layer 20 is joined to a lower joining area 34 of the platform 14 by means of a structural adhesive connection 36. Generally, a structural adhesive forms a permanent composite which can be dismantled only destructively, whereas the dry-bond adhesive of the plaster coating 28 can be construed reversible. As a rule of thumb, pressure sensitive adhesives have a maximum shear strength of approximately 0.3 N/mm$^2$, and structural adhesives start at approximately 1 N/mm$^2$ and preferably have more than 2 N/mm$^2$ shear strength. For this purpose structural adhesives in the form of epoxide resin, cyanoacrylate and polyurethane-adhesives should be considered. Pressure sensitive adhesive coatings for plasters are known per se, e.g., in the form of high-molecular acrylate polymers. Further details of such structural and pressure sensitive adhesives are given in U.S. Publication No. 2016/0213322, which is incorporated by reference herein.

As shown in different embodiments in FIGS. 3 to 9, the structural adhesive 36 is applied as a bead along predefined adherend lines or tracks 38 in the joining area 34 between the platform 14 and the carrier layer 20. Thereby, the bonding is reduced to one-dimensional paths, which are arranged in a specific pattern in the joining area 34 in order to allow the skin 30 to stretch freely and to breathe while preserving a high cohesiveness only where necessary.

Figure 3:
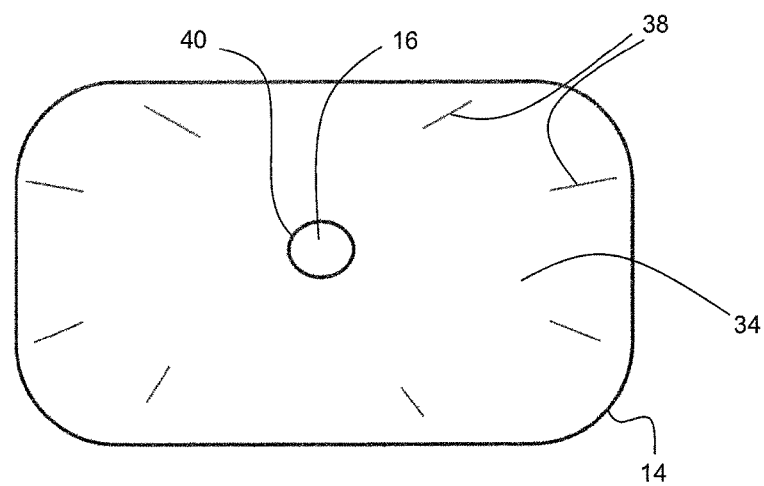
FIGS. 3 to 9 show a bottom view of a joining area of the platform provided with adherend tracks for connection to the plaster in different embodiments.

In the embodiment of FIG. 3, the tracks 38 are arranged at a distance to the access port 16 and run in a star-like configuration only in a boundary range of the joining area 34. A further circularly closed adherend track 40 is formed circumferentially around the access port 16. Generally, the adherend tracks 38, 40 may be configured as continuous lines or dot-dashed lines or line of points.

Figure 4:
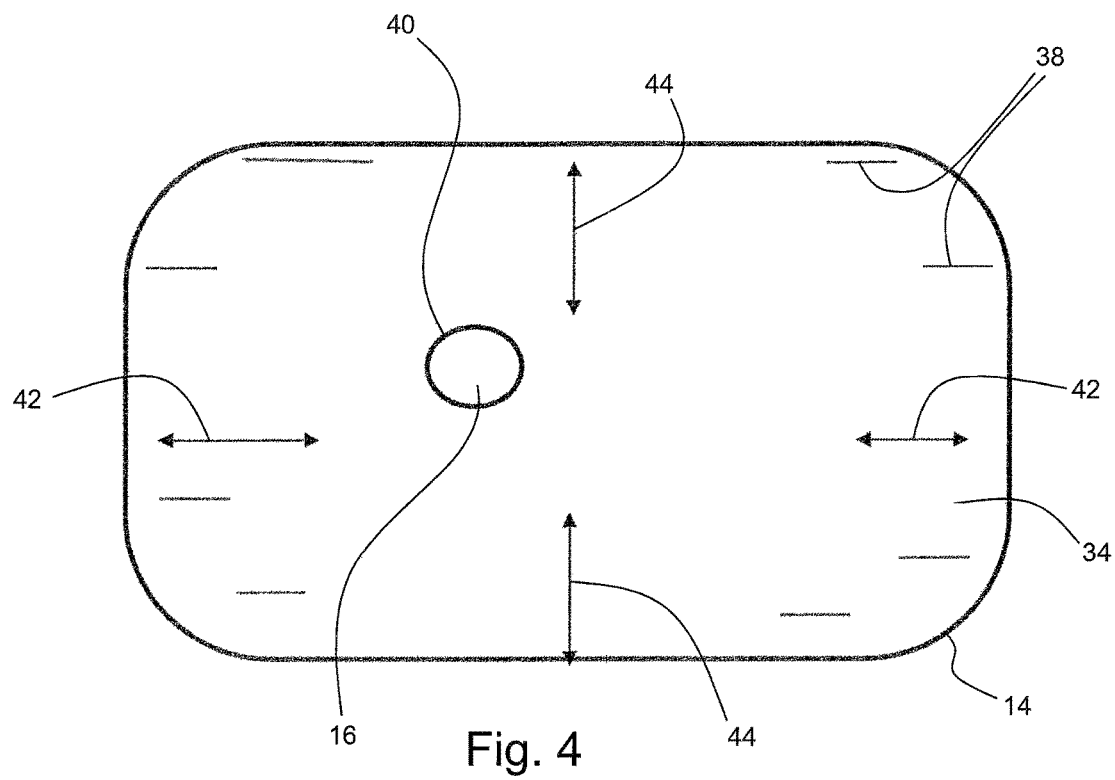

FIG. 4 shows an alternative in which the tracks 38 are arranged in the longitudinal end sections and extend parallel to the longitudinal direction of the plaster 14, thus allowing for a stretchability of the carrier layer 20 which is increased in the longitudinal and transverse directions as illustrated by arrows 42, 44. The increased breath- or stretchability in the preferred directions is supported when aligning the warp and weft threads of the carrier layer fabric in direction of arrows 42, 44.

Conveniently, when the carrier layer 34 has an anisotropic elasticity, a preferred direction of increased stretchability induced by the arrangement of the adherent tracks 38, 40 should be oriented in direction of the increased elasticity. Then, the adhesiveness of the coating 28 is less impaired by rigid fixation patterns.

A further improvement in the adhesive power of the plaster 12 can be achieved when the preferred direction of increased stretchability of the carrier layer 34 is provided in the main direction of skin elongation at the site of application on the body. For example, in the area of the abdomen the daily movements cause a significant higher skin stretching in longitudinal direction of the body as compared to the body transverse axis. Such a skin stretching, due to the provoked shear stresses in the plaster 12, has a large impact on the possible wearing time of the device on the body.

If the plaster 12 has a preferred stretching direction, the best orientation on the body should be achieved by mostly intuitive handling. Then, it should be guaranteed that the design of the carrier system assists the user. For such purpose, marker arrows 46 may indicate a preferred orientation with respect to a body axis (cp. FIG. 1).

Figure 5:
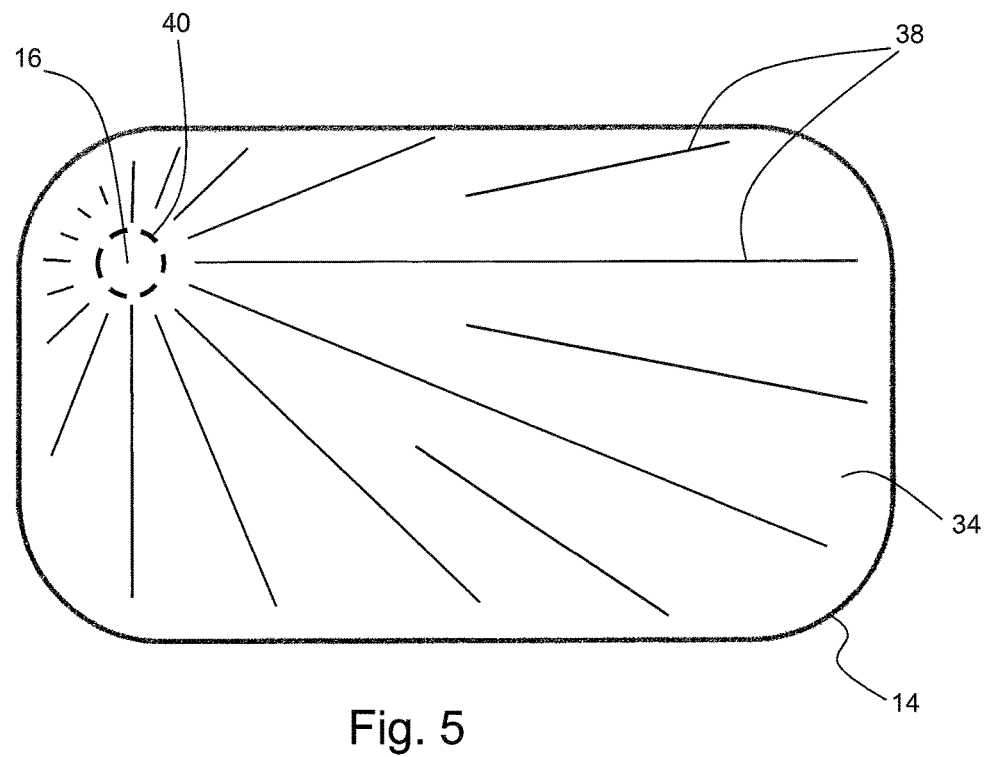

FIG. 5 shows another preferred example of possible arrangements of the adherend tracks 38, 40, along which the structural adhesive is applied in the form of beads. In this case, the access port 16 is positioned eccentrically on the joining area 34 and is surrounded by a dashed circular track 40. Further tracks 38, which may be disrupted in sections, extend in radial directions. In this configuration, an increased stretchability is achieved in the transverse direction of the platform 14.

Figure 6:
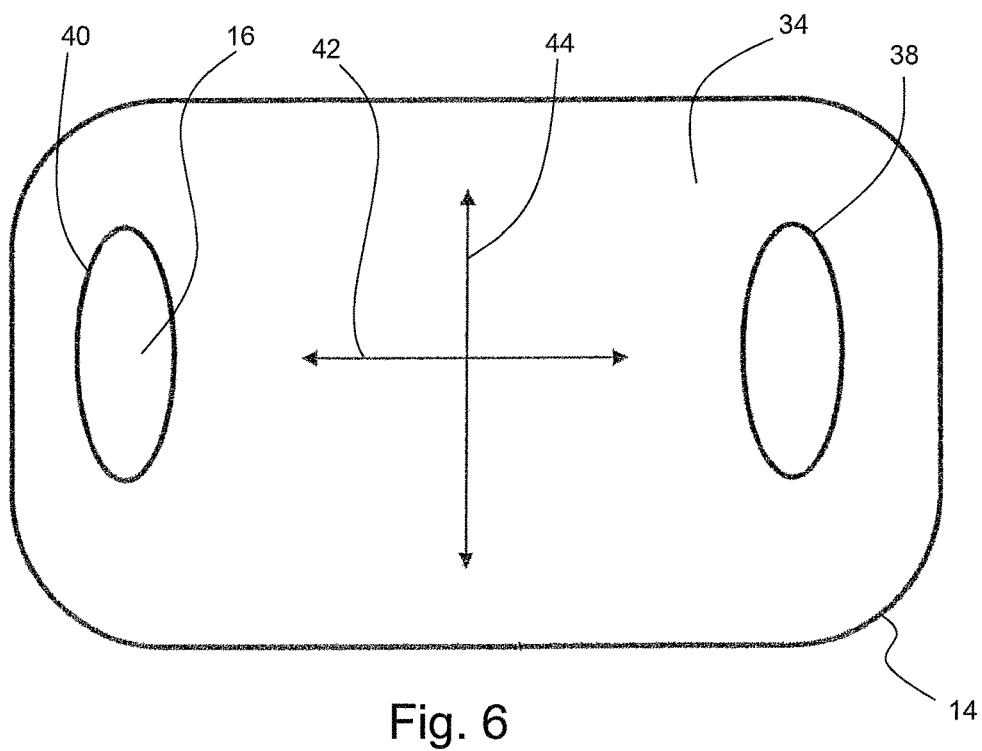
Figure 7:
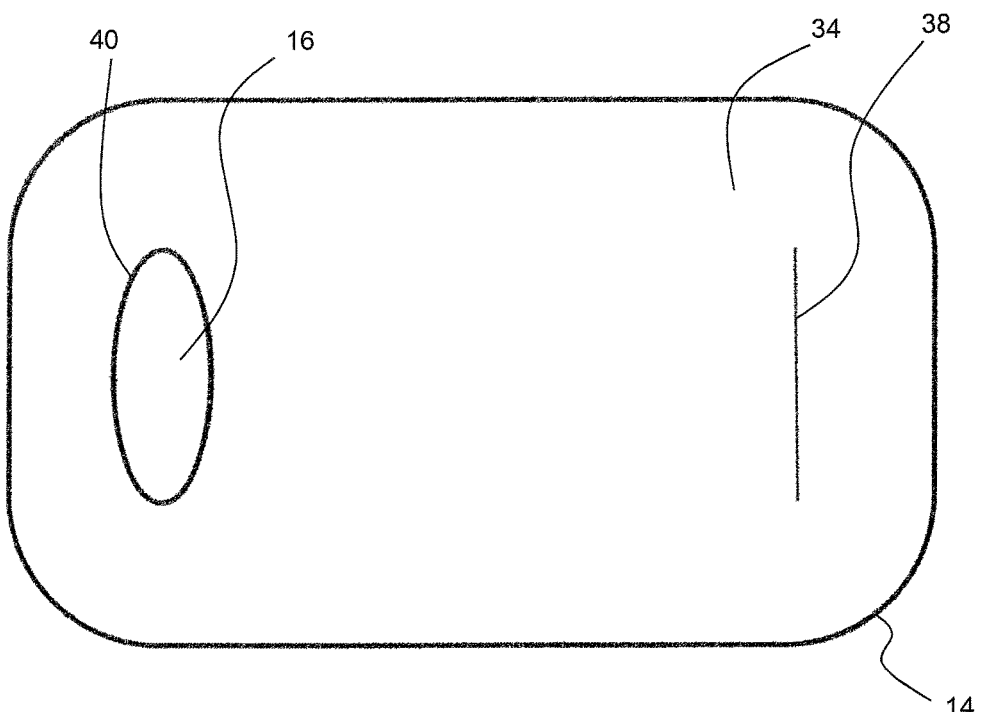

In the embodiment of FIG. 6, the access port 16 has an oval configuration and is arranged in the left half of the platform 14, while another oval shaped track 38 is positioned symmetric to the center of the joining area 34 in the right half. Again, increased stretchability is achieved in longitudinal and transverse directions as illustrated by arrows 42, 44. FIG. 7 shows a similar arrangement in which a linear track 38 is positioned opposite to track 40 surrounding the access port 16.

Figure 8:
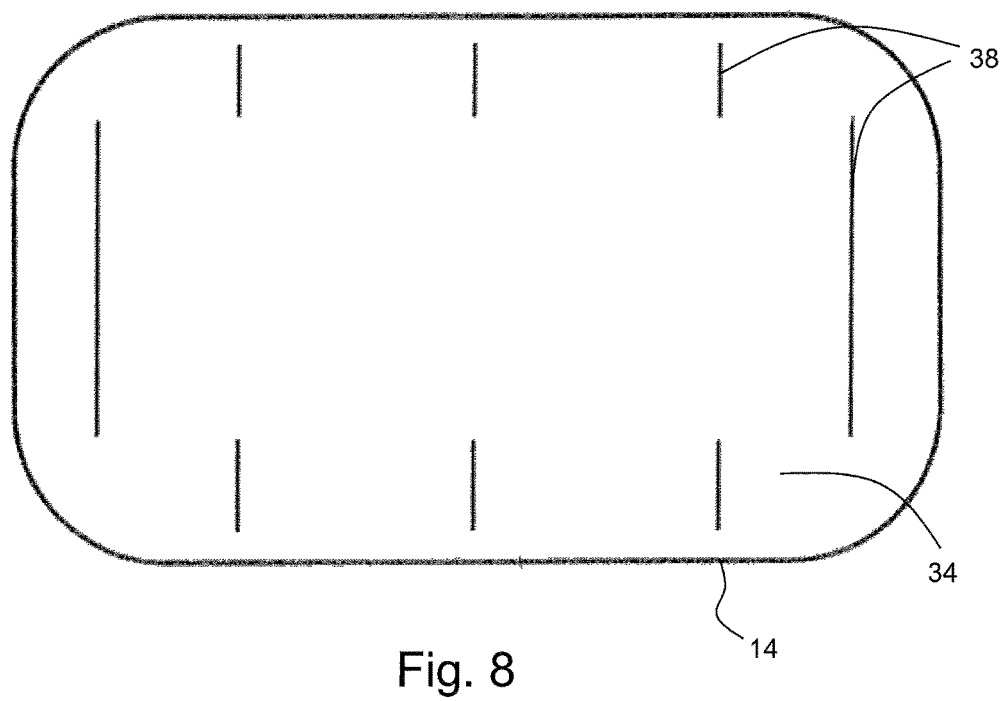
Figure 9:
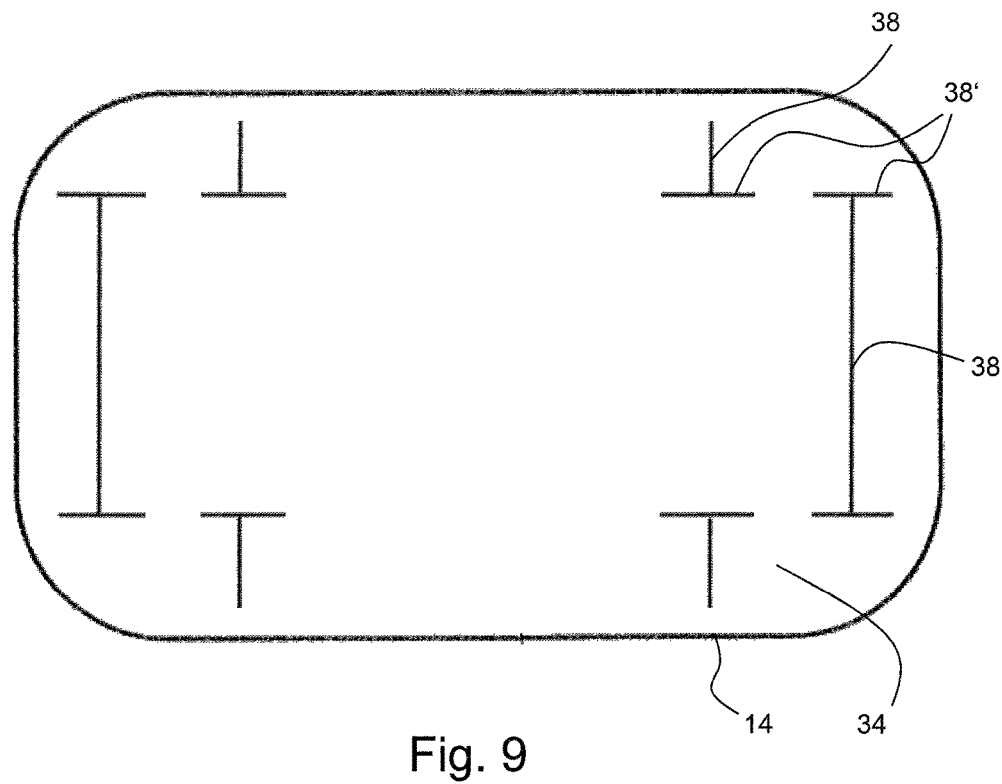

In the embodiment of FIG. 8, the tracks 38 are arranged only in the boundary of the joining area 34 (similar to FIG. 4) and extend transverse to the longitudinal direction of the plaster 14, thereby preserving stretchability in the longitudinal direction. A further improvement in the joint strength may be achieved by an embodiment according to FIG. 9, where the transverse tracks 38 are arranged similar to FIG. 8, but are terminated at least on one side by short longitudinal tracks 38'.

In order to further improve breathability, it is also beneficial when the base of the platform 14 is perforated or includes a membrane material.

It goes without saying that the platform 14 and the joining area 34 need not be rectangular, but can assume different geometric shapes depending on the intended application.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A carrier system for use with a medical device worn on the body, the carrier system comprising:
    a substantially flat carrier layer;
    a pressure sensitive adhesive coating on an underside of the carrier layer, the pressure sensitive adhesive coating configured to adhere to the skin of a body part;
    a dimensionally stable platform positioned on an upper side of the carrier layer, the platform having adherend tracks arranged in a predefined pattern on a bottom side thereof; and
    a structural adhesive disposed along the adherend tracks and forming paths corresponding to the predefined pattern;
    wherein the adherend tracks and structural adhesive form a joining area of the platform which is joined to the upper side of the carrier layer.

2. Carrier system according to claim 1, wherein the adherend tracks comprise continuous lines, dot-dashed lines or lines of points.

3. Carrier system according to claim 1, further comprising an access port in the platform which is configured to be open to the skin through the carrier layer.

4. Carrier system according to claim 3, wherein one of the adherend tracks is formed circumferentially around the access port.

5. Carrier system according to claim 3, wherein one or more of the adherend tracks has a radial or star-shape as viewed from the access port.

6. Carrier system according to claim 3, wherein at least one of the adherend tracks is arranged at a distance from the access port and/or runs only in a boundary range of the joining area.

7. Carrier system according to claim 3, wherein the access port and a circular or line-shaped one of the adherend tracks are arranged at a distance to each other in different regions of the joining area.

8. Carrier system according to claim 7, wherein the access port and the circular or line-shaped one of the adherend tracks are arranged symmetric to the center of the joining area.

9. Carrier system according to claim 1, wherein the adherend tracks are positioned on the joining area such that the carrier layer preserves a stretchability in at least one direction.

10. Carrier system according to claim 1, wherein the carrier layer has an anisotropic elasticity, and a direction of increased stretchability resulting from the arrangement of the adherent tracks.

11. Carrier system according to claim 1, wherein a direction of increased stretchability of the carrier layer is configured to coincide with a main direction of skin elongation at an application site on the body.

12. Carrier system according to claim 1, further comprising a marker configured to indicate a preferred orientation of the carrier layer to a user.

13. Carrier system according to claim 1, wherein the carrier layer has a circumferential border section which protrudes by at least 4 mm over a lateral margin of the joining area.

14. Carrier system according to claim 1, wherein the structural adhesive has a shear strength of more than 1 $N/mm^2$.

15. Carrier system according to claim 1, wherein the structural adhesive is formed by one of epoxide resin, cyanoacrylate and polyurethane-adhesives.

16. Carrier system according to claim 1, wherein the structural adhesive forms a permanent composite which can only be destructively dismantled.

17. A method of using a carrier system according to claim 1, comprising adhering the carrier system to the skin of a user such that a direction of increased stretchability of the carrier layer is oriented in the main direction of skin elongation at the application site on the body.

18. A method of using a carrier system according to claim 1, comprising at least one of the following steps:
    (a) sensory control or detection of a body parameter;
    (b) application of agents, specifically insulin through or to the skin; and
    (c) providing access to the body.

19. A method of assembling a carrier system for use with a medical device worn on the body, comprising the following steps:
    providing a substantially flat carrier layer having a pressure sensitive adhesive coating on an underside thereof, the pressure sensitive adhesive coating configured to adhere to the skin of a body part;
    providing a dimensionally stable platform having adherend tracks arranged in a predefined pattern on a bottom side thereof;
    applying a structural adhesive as a bead along the adherend tracks; and
    positioning the platform on an upper side of the carrier layer, wherein the adherend tracks and structural adhesive form a joining area of the platform which is joined to the upper side of the carrier layer.

20. The method of claim 19, further comprising adhering the carrier system to the skin of a user such that a direction of increased stretchability of the carrier layer is oriented in the main direction of skin elongation at the application site on the body.

* * * * *